United States Patent [19]

Kurobane et al.

[11] 4,424,373
[45] Jan. 3, 1984

[54] SECALONIC ACIDS

[75] Inventors: Itsuo Kurobane, Madison, Wis.; Leo C. Vining; Alister G. McInnes, both of Halifax, Canada

[73] Assignee: Asahi Kasei Kogyo Kabushiki Kaisha, Osaka, Japan

[21] Appl. No.: 407,100

[22] Filed: Aug. 11, 1982

Related U.S. Application Data

[63] Continuation of Ser. No. 113,664, Jan. 21, 1980, abandoned.

[30] Foreign Application Priority Data

Jan. 30, 1979 [JP] Japan ................................. 54-8774

[51] Int. Cl.³ .......................................... C07D 311/86
[52] U.S. Cl. .................................. 549/393; 424/278
[58] Field of Search ....................................... 549/393

[56] References Cited

PUBLICATIONS

J. Hooper et al., J. Chem. Soc. (C) (1971), pp. 3580-3590.
J. W. ApSimon et al., J. Chem. Soc., (1965), pp. 4144-4157.
Yosioka, I. et al., Chem. Pharm. Bull. (1968), vol. 16, pp. 2090-2091.
Aberhart, D. J., et al., Tetrahedron (1965), vol. 21, pp. 1417-1432.
B. Franck et al., Angew. Chem. Internat. Edn. (1964), vol. 3, pp. 441-442.
B. Franck et al., Chem. Ber. (1966), vol. 99, pp. 3842-3863.
P. Steyn, Tetrahedron (1970), vol. 26, pp. 51-57.
M. Yamazaki et al., Chem. Pharm. Bull. (1971), vol. 19, pp. 199-201.
I. Yosioka et al., Chem. Pharm. Bull. (1972), vol. 20, pp. 1082-1084.
C. Howard et al., J. Chem. Soc. Comm. (1973), p. 464.
C. Howard et al., J. Chem. Soc. Perkin I (1973), pp. 2440-2444.
R. Andersen et al., J. Org. Chem. (1977), vol. 42, pp. 352-353.
C. Howard et al., J. Chem. Soc. Perkin I (1976), pp. 1820-1822.

*Primary Examiner*—Norma S. Milestone
*Attorney, Agent, or Firm*—Finnegan, Henderson, Farabow, Garrett & Dunner

[57] ABSTRACT

Secalonic acids having a 2,4'-linkage of the formula (I) or a 4,4'-linkage of the formula (II).

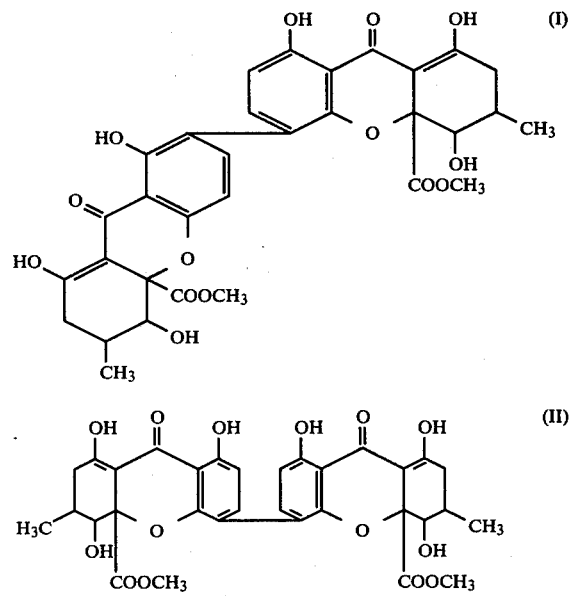

5 Claims, 13 Drawing Figures

SECALONIC ACIDS

This is a continuation of application Ser. No. 113,664 filed Jan. 21, 1980, now abandoned.

BACKGROUND OF THE INVENTION

1. Field of the Invention

This invention relates to novel secalonic acids having a 2,4'-linkage or a 4,4'-linkage and a method of their preparation.

2. Description of the Prior Art

Seven kinds of secalonic acids having a different structure such as secalonic acid A, B, C, D, E, F and G are isolated from fungi or Lichens and are reported by the following literature.

(1) Isolation of secalonic acids A, B and C from *Claviceps purpurea* (B. Frank and E. M. Gottshalk, Angew. Chem. Internat. Edn., 1964, 3, 441; B. Frank, E. M. Gottshalk, U. Ohnsorge and F. Hüper, Chem. Berl., 1966, 99, 3842; D. J. Abehart, Y. S. Chen, P. de Mayo and J. B. Stothers, Tetrahedron, 1965, 21, 1417).

(2) Isolation of secalonic acids A and B from *Penicillium islandicum* (J. W. Apsimon, J. A. Corran, N. G. Greasey, W. Marlow, W. B. Whalley and K. Y. Sim, J. Chem. Soc., 1965, 4144).

(3) Isolation of secalonic acid A from *Parmelia entotheiochroa* (I. Yoshioka, T. Nakanishi, S. Izumi and I. Kitagawa, Chem. Pharm. Bull., 1968, 16, 2090).

(4) Isolation of secalonic acid D from *Penicillium oxalicum* (P. W. Steyn Tetrahedron, 1970, 26, 51).

(5) Isolation of secalonic acid A from *Aspergillus ochraceus* (M. Yamazaki, Y. Maebayashi and K. Miyaki, Chem. Pharm. Bull., 1971, 19, 199).

(6) Isolation of secalonic acid C from *Cetraria ornate* (I. Yoshioka, H. Yamauchi, K. Murata and I. Kitagawa, Chem. Pharm. Bull., 1972, 20, 1082)

(7) Isolation os secalonic acid A, E and G from *Pyrenochaeta terrestris* (C. C. Howard, R. A. W. Johnston and I. D. Entwistle, J. Chem. Soc. Comm., 1973, 464; C. C. Howard and R. A. W. Johnstone, J. Chem. Soc. Perkin I, 1973, 2440; I. Kurobane, L. C. Vining and A. G. McInnes, Tetrahedron Letters, in press).

(8) Isolation of secalonic acids D and F from *Aspergillus aculeatus* (R. Andersen, G. Büchi, B. Kobbe and A. L. Demain, J. Org. Chem. 1977, 42, 352).

All of these seven secalonic acids are dimer. The dimer firstly had been considered to have a 4,4'-linkage by a mistake of fact. But now, it is confirmed that the dimer has a 2,2'-linkage. Namely, C. C. Howard et al. completely proved this fact by analyzing secalonic acid A crystals by X-ray diffractiometry (J. Chem. Soc. Perkin I, 1976, 1820-1822).

And J. W. Hooper et al. proved the linkages of all the secalonic acids A, B, C and D are 2,2'-linkages by $^1$H-nuclear magnetic resonance (J. Chem. Soc. (c), 1971, 3580-3590).

Further, Itsuo Kurobane et al. proved by $^{13}$C-nuclear magnetic resonance that secalonic acids E and G have the same 2,2'-linkage as secalonic acid A, secalonic acid D is an enantiomer having the same linkage as secalonic acid A, and secalonic acid F is also an enantiomer having the same linkage as secalonic acid G. Thus, all seven secalonic acids which have been isolated until now have 2,2'-linkage.

SUMMARY OF THE INVENTION

An object of this invention is to provide novel secalonic acids having a 2,4'-linkage or a 4,4'-linkage.

Another object of this invention is to provide a method of preparing novel secalonic acids.

A further object of this invention is to provide a novel antibacterial agent.

Accordingly, the present invention in one embodiment provides secalonic acids having a 2,4'-linkage of the formula (I),

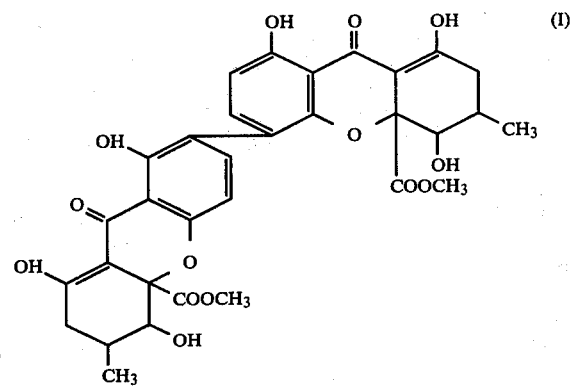

The present invention in another embodiment provides secalonic acids having a 4,4'-linkage of the formula (II),

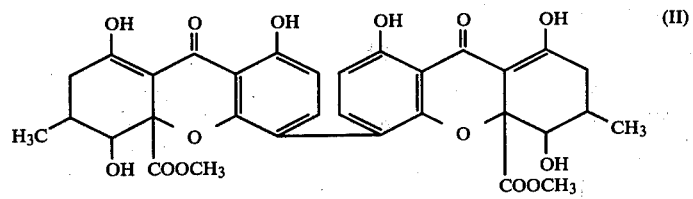

In a further embodiment, the present invention provides a method of preparing the compound of the formula (I) or (II) as described above which comprises dissolving known secalonic acids having a 2,2'-linkage of the formula (III),

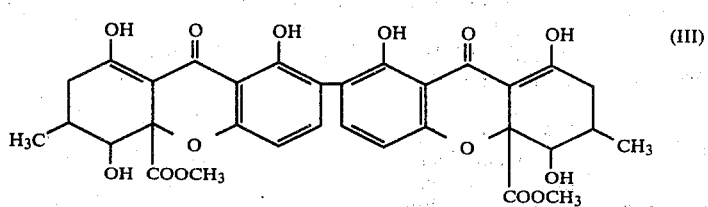

(III)

into a polar organic solvent and leaving to stand the solution till an optical rotation of the solution shows a constant value.

In a still further embodiment, the invention provides a method of preparing the compound of the formula (I) or (II) as described above which comprises melting the secalonic acids of the formula (III) under heating in the absence of a solvent.

DETAILED DESCRIPTION OF THE INVENTION

Rearrangement of the linkage of the secalonic acids will now be explained by the following example where known secalonic acid A or D is used as a starting material and pyridine is used as a polar organic solvent.

Secalonic acid A having a 2,2'-linkage was dissolved into pyridine and the solution was left to stand at room temperature. A small amount of the solution was corrected with the passage of time and developed on a thin layer chromatography such as Silica Gel 60F-254. Two kinds of compounds were obtained. The compound which was first obtained was confirmed to be secalonic acid A having a 2,4'-linkage and the other compound subsequently obtained was conformed to be secalonic acid A having a 4,4'-linkage by the method as will be described below.

Rf value of secalonic acid A having a 2,2'-linkage, "Compound I", secalonic ascid A having a 2,4'-linkage, "Compound II" and secalonic acid A having a 4,4'-linkage, "Compound III", obtained by using a mixed solvent of benzene and ethyl acetate (volume ratio: 3:1) as a developing agent, were 0.15, 0.08 and 0.42, respectively.

Compound II was separated and dissolved into pyridine. After leaving the solution to stand at room temperature, a part of Compound II changed to Compound I and Compound III. Similarly, a part of Compound III dissolved into pyridine changed to Compound II and subsequently changed to Compound I. After these changes were occurred, the solution was continued to be left to stand at room temperature, but no further change was observed. The amount of each of Compounds I, II and III was equal.

Figure 8:
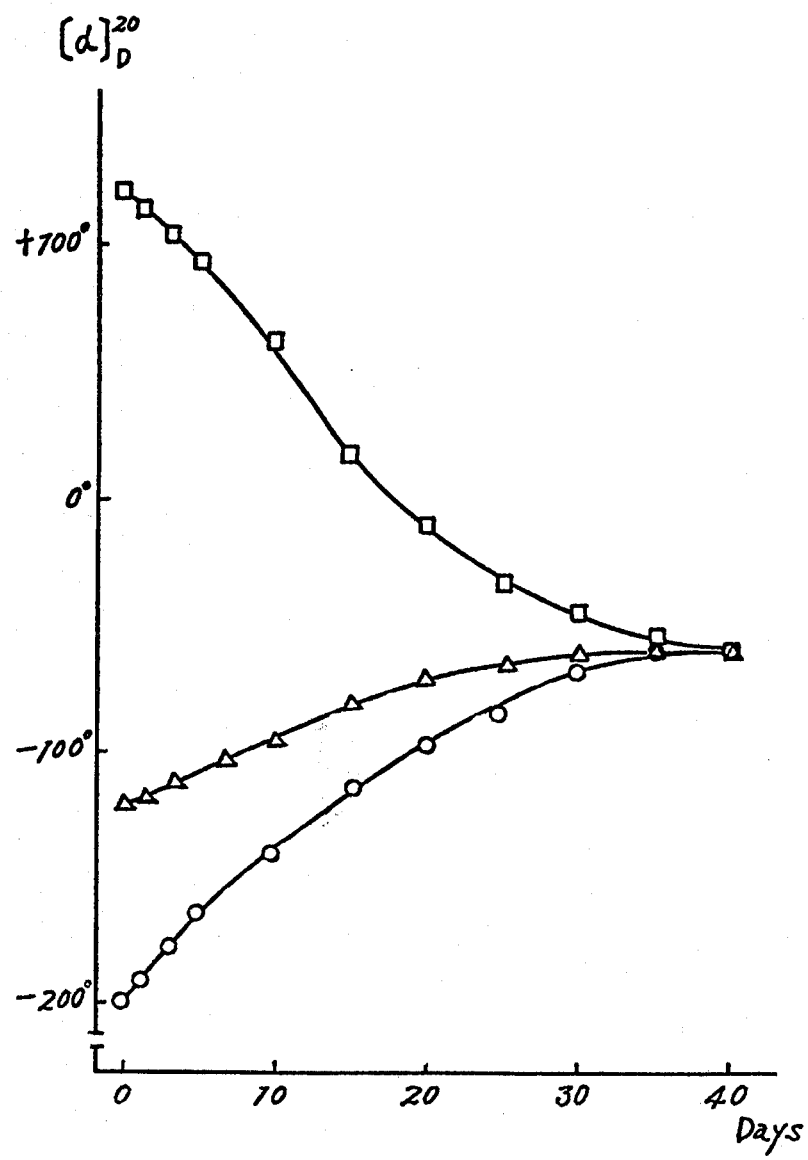
FIGS. 8, 9 and 10 are graphs showing the relationship of the specific rotatory power of each secalonic acid in pyridine with the period of time for operation.
Figure 9:
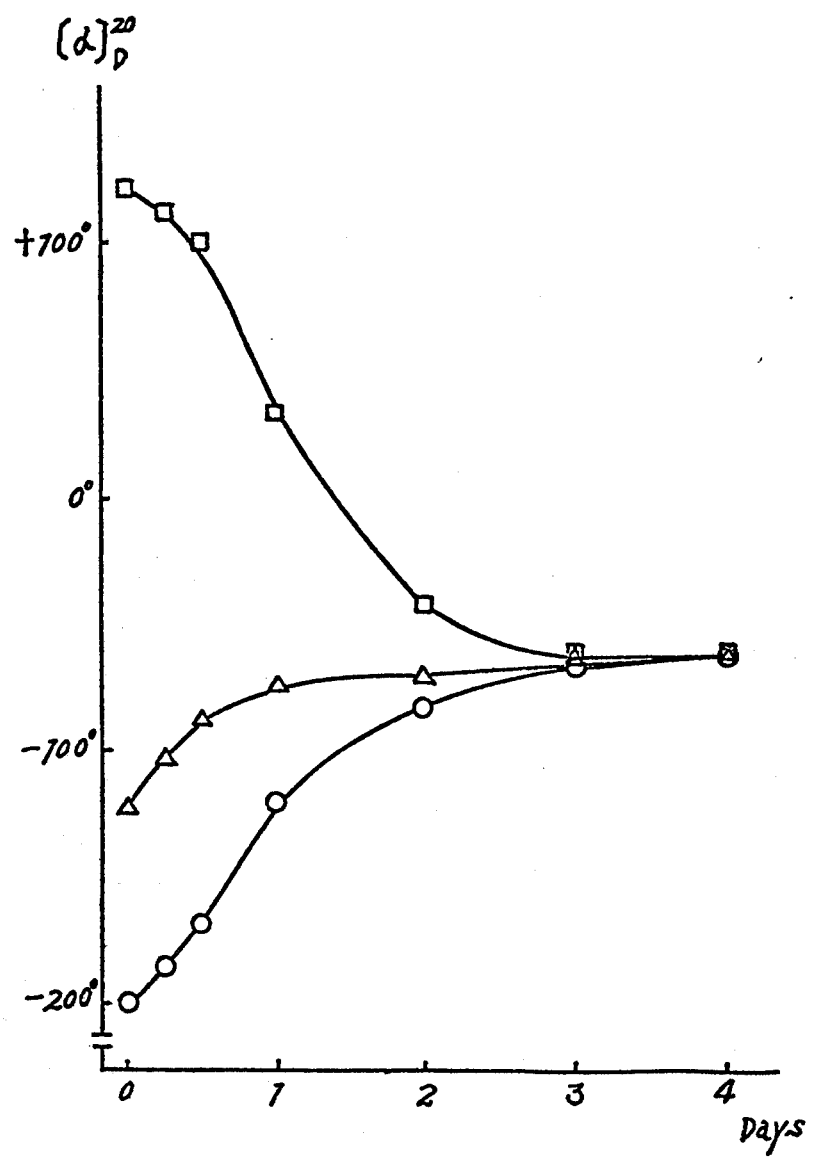
Figure 10:
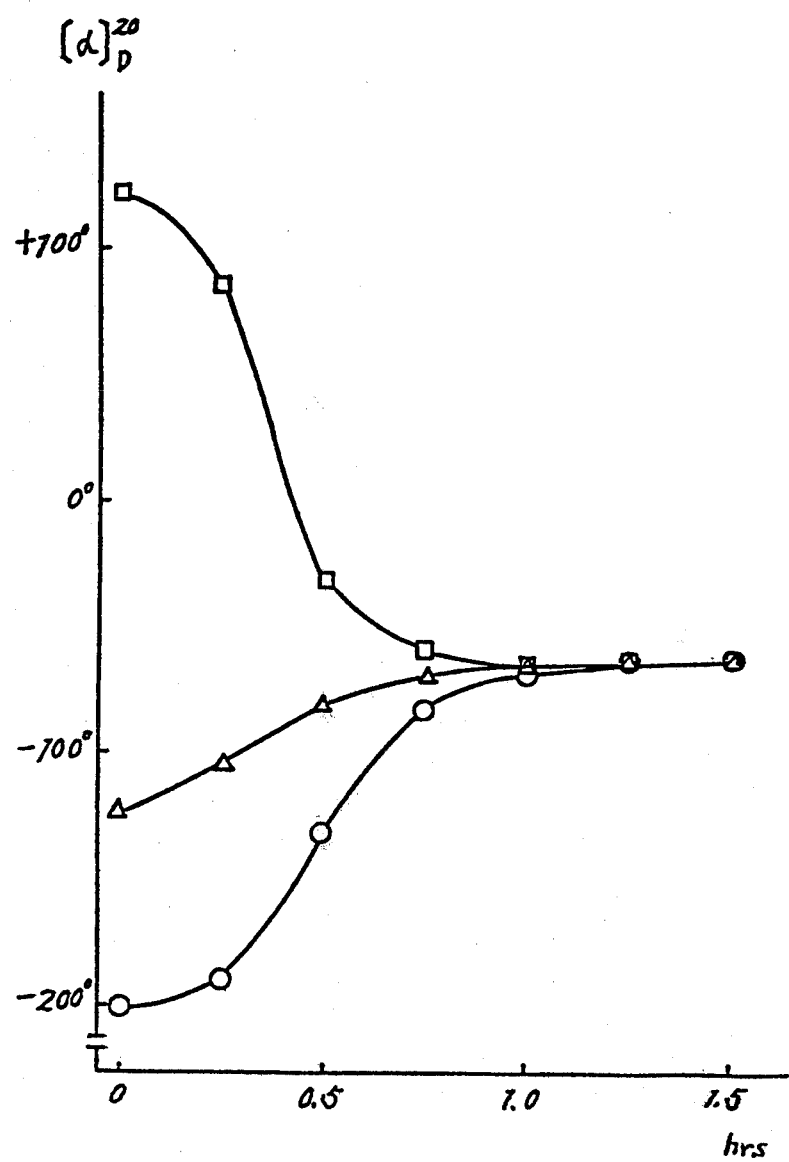

Then, Compounds I, II and III were dissolved into pyridine at the concentration of 1% by weight. After the mixed solutions were left to stand at 25° C., 45° C. and 95° C., respectively, the specific rotatory power was measured with the period of time for operation by a sodium lamp. During the measurement, the sample in the tube was kept at 20° C. under cooling with cold water. FIG. 8, FIG. 9 and FIG. 10 show the change of the specific rotatory power of the solution left to stand at 25° C., 45° C. and 95° C., respectively. As shown by these Figures, each value of the optical rotation of Compounds I to III in pyridine changed with time from the primary value of $-200.1°$, $-110.9°$ and $+125.7°$ to a constant value of about $-62°$. This value is approximate to the average specific rotatory power of above three compounds, $-61.8°$. Accordingly, this shows that the mixed solution is consisting of the same amount of three compounds and equilibrium. The period of time to reach the equilibrium depends on the temperature employed, and is about 35 days at 25° C., about 3.5 days at 45° C. and about one hour and fifteen minutes at 95° C., respectively.

The same experiment as described above was carried out by using 2,2'-linked secalonic acid D which was enantiomer of 2,2'-linked secalonic acid A, and as a result, the same change was observed and the change of specific rotatory power was also the same within the experimental errors.

The novel Compound V which is firstly obtained from 2,2'-linked secalonic acid D by the thin layer chromatography is secalonic acid D having a 2,4'-linkage, and the novel Compound VI which is subsequently obtained by the thin layer chromatography is secalonic acid D having a 4,4'-linkage.

Figure 11:
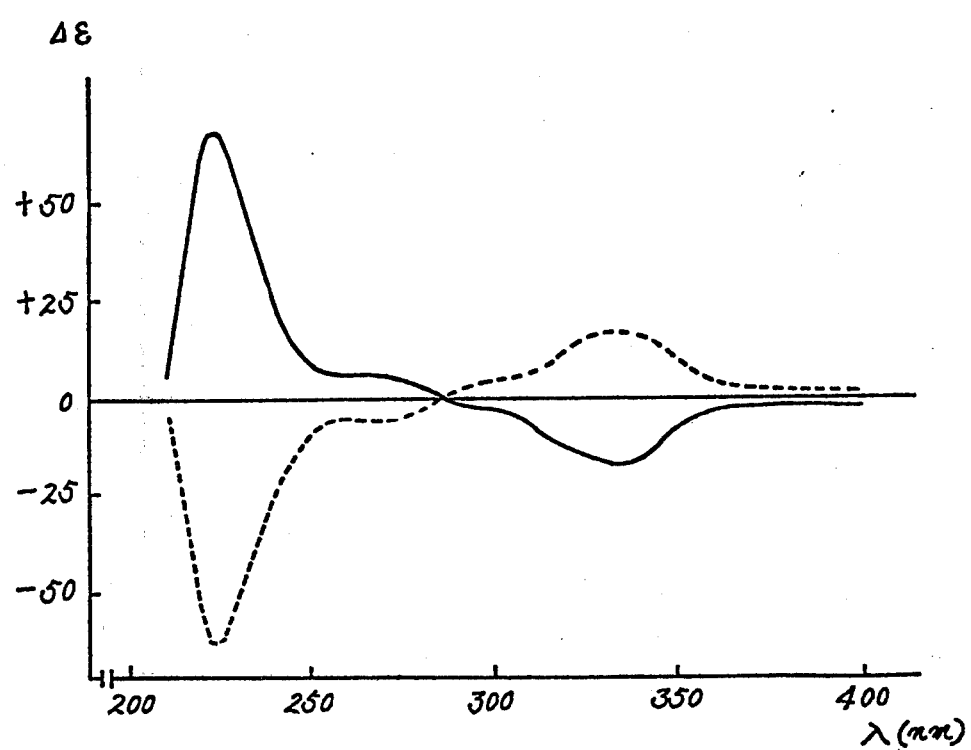
FIGS. 11, 12 and 13 are graphs showing the molar circular dichroic absorbancy index of each secalonic acid with the wave length.
Figure 12:
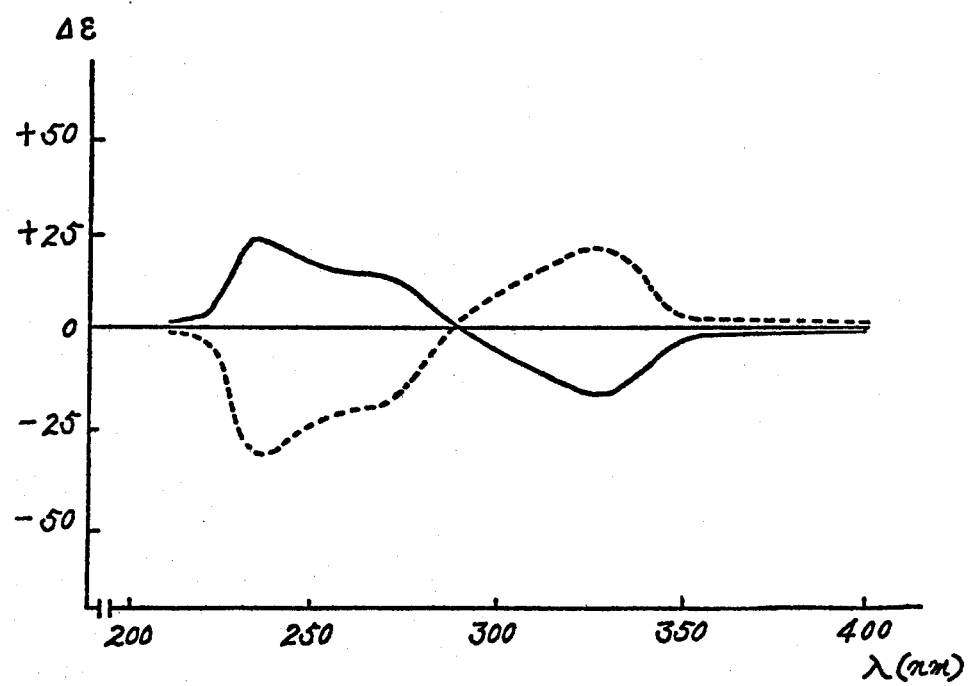
Figure 13:
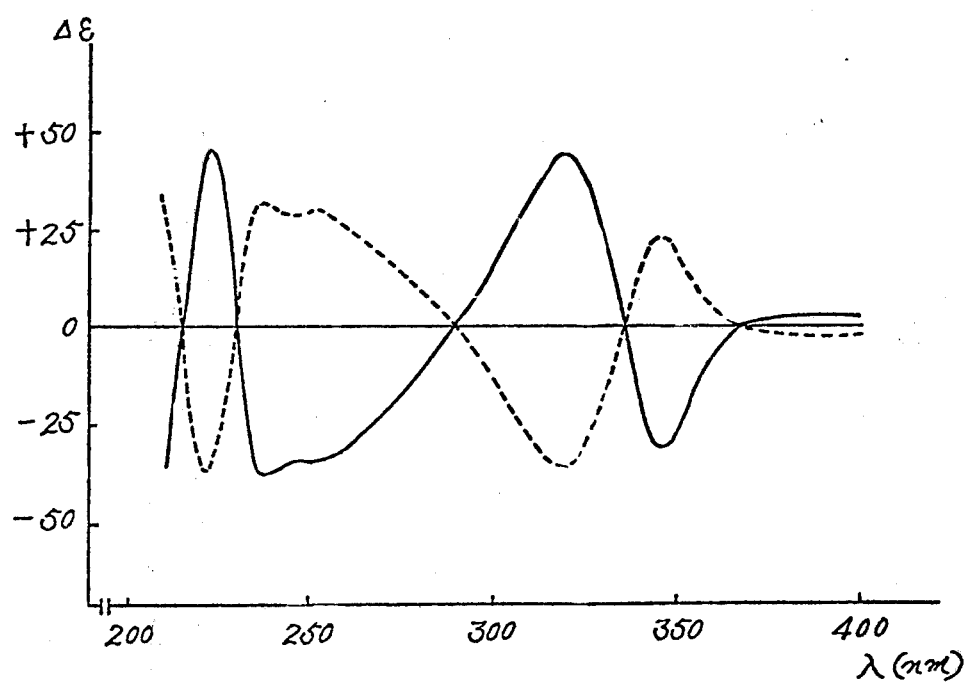

FIGS. 11, 12 and 13 show the circular dichroism spectra of each of these secalonic acids measured in dioxane, and it is found from the Figures that Compounds I, II and III are the enantiomers of Compounds IV, V and VI, respectively.

The linkages of secalonic acids B, C, E, F and G can be rearranged in the same method as described above.

2,2'-Linked secalonic acid A was dissolved in 32 types of organic solvents and 11 types of inorganic bases and acids to examine whether the structural changes of secalonic acids, as the change as observed in pyridine, occur in these solvents. As a result, the same structural changes of secalonic acids were also occurred in organic solvents such as acetone, N,N-dimethylformamide, dimethyl sulfoxide and acetonitrile.

Compound I was dissolved in acetone, N,N-dimethylformamide and dimethyl sulfoxide to give a 0.2% solution, respectively, and Compound I was dissolved in acetonitrile to give a 0.03% solution. Compound III was dissolved in the above described four solvents in the same manner as Compound I. These solutions were left to stand at room temperature and the change of the specific rotatory power of each solution was observed with the passage of time to find the time when the specific rotatory powers of Compound I and Compound III reached the same value within the experimental error. The periods of time to reach the equilibrium were observed and was about 40 days in acetone, 2.5 days in acetonitrile, about 1 day in N,N-dimethylformamide and 0.75 day in dimethyl sulfoxide, respectively. The periods of time to reach the equilibrium also depended on the temperature employed as in pyridine, and were 3.5 days in acetone, 6 hours in acetonitrile, about 3 hours in N,N-dimethylformamide and about 2 hours in dimethyl sulfoxide at 45° C.

Another method of rearranging the linkage of the secalonic acids is to melt the secalonic acid under heating without using any solvent. This example is given below.

In a glass tube having a small diameter were placed 988 mg of 2,2'-linked secalonic acid A and the tube was sealed under a reduced pressure of not higher than $10^{-3}$ mmHg by a vacuum pump. The tube was placed in a electric oven, and the tube was heated for 25 minutes at 280° C. and further for 5 minutes to completely melt the secalonic acid. Subsequently, the tube was left to stand at room temperature for cooling, and then the secalonic acid was taken out of the tube and dissolved in ethyl acetate. The product was purified by column partition chromatography which will be explained below with three kinds of products. These products were confirmed to be the same compounds of Compound I, II and III as described above. The yields of Compound I, II and III were 223 mg, 217 mg and 204 mg, respectively.

In this experiment, the yields of Compound I, II and III were decreased when the tube was sealed without reducing pressure, because a large amount of dark brown compound which might be caused by the oxidation reaction was produced. Further, when the secalonic acid was not heated nor melted sufficiently even under vacuum, a large amount of Compound I remains unreacted, resulting in a small amount of Compounds II and III. In contrast with this, when the secalonic acid was overheated, a brownish orange compound which might be caused by the thermal decomposition was produced and the yields of Compounds I, II and III were decreased.

Rearrangement of the linkage by heating was observed with other secalonic acids. The linkage of each secalonic acid can be remarkably rearranged on heating the secalonic acid to melt under vacuum.

In all cases, the products are obtained as a mixture with the starting material, therefore the product must be purified. Chromatography can be employed for the purification, and column partition chromatography is preferred. The example of the purification method is given below.

1.006 g of secalonic acid A having 2,2'-linkage (Compound I) were dissolved in 20 ml of pyridine. After the solution was left to stand for 4 days at 45° C., the pyridine was removed by a reduced pressure distillation and the removal was completed in a desiccator under reduced pressure for all day. The product obtained in the above described step was dissolved under heating in a small amount of ethyl acetate and the solution was contacted with silicic acid powder. After the solution was adsorbed on silicic acid powder, the powder was left to stand at 45° C. to evaporate the ethyl acetate. Then the powder was suspended in benzene and the suspension was pored in a column filled with silicic acid. A mixed solvent of benzene and ethyl acetate was used as a developing agent. Compound III was eluted when the volume ratio of benzene to ethyl acetate was 4:1, Compound I was eluted when the volume ratio was 2:1 and Compound II was obtained when the volume ratio was 1:1. Then Compounds II and III were recrystallized from ethanol and Compound I was recrystallized from a 2:1 volume ratio mixed solution of ethyl acetate and ethanol. The yields of Compounds I, II and III were 292 mg, 297 mg and 281 mg, respectively.

Also other secalonic acids can be purified by the same method as described above. For example, 430 mg of secalonic acid D having a 2,2'-linkage (Compound IV) were dissolved in 10 ml of pyridine and the solution was left to stand for 4 days at 45° C., and then purified by the same method as described above to give Compounds IV, V and VI. The yields of Compound IV, V and VI were 136 mg, 138 mg and 133 mg, respectively.

Table 1 shows various physical properties of the above described Compounds I to VI.

Table 2 shows chemical shifts ($\delta c$, TMS) of Compounds I to VI in deuterium substituted pyridine.

Tables 3-1 and 3-2 show coupling constants ($J_{CH}$, Hz) of carbonhydrogen linkage in Compounds I to VI in deuterium substituted pyridine.

Table 4 shows coupling constants of $^{13}C$-$^{13}C$ spin-spin couplings in Compounds I and III.

Tables 5-1 and 5-2 show the deuterium isotope effect on $^{13}C$ chemical shifts of Compound III and Compound VII, i.e. the formyl derivative of Compound I, in deuterium substituted chloroform.

TABLE 1

| | Compound Number | | |
|---|---|---|---|
| | I | II | III |
| Melting Point (°C.) | 208~209 | 200~201 | 204~205 |
| Mass | 638.1649 | 638.1617 | 638.1642 |
| | 579.1506 | 579.1494 | 579.1511 |
| $[\alpha]_D^{20}$ (pyridine) (°) | −200.1°(c 0.275) | −110.9°(c 0.289) | +125.7°0.285) |
| $\lambda_{max}^{dioxane}$ | 239(4.24) | 251(4.27) | 255(4.37) |
| nm (log $\epsilon$) | 267(4.19) | 264(4.25) | 338(4.47) |
| | 338(4.51) | 338(4.51) | |
| $\nu max$ cm$^{-1}$ (KBr) | 3550(free OH) | 3550(free OH) | 3580(free OH) |
| | 3450(H-bonded OH) | 3450(H-bonded OH) | 3450(H-bonded OH) |
| | 1735(aliphatic C=O) | 1750(aliphatic C=O) | 1750(aliphatic C=O) |
| | 1605(H-bonded C=O) | 1735(aliphatic C=O) | 1615(H-bonded C=O) |
| | | 1610(H-bonded C=O) | |

TABLE 1-continued

| | Compound Number | | |
|---|---|---|---|
| ¹H—NMR(pyridine) | 1.26(d,J6.0,H-11,11')<br>2.2–2.9(m,H-6,6',7,7')<br>3.57(s,H-13,13')<br>4.18(d,J10.5,H-5,5')<br>6.68(d,J8.5,H-4,4')<br>7.58(d,J8.5,H-3,3') | 1.14(d,J6.0,H-11')<br>1.25(d,J6.0,H-11)<br>2.1–2.9(m,H-6,6',7,7')<br>3.34(s,H-13)<br>3.58(s,H-13')<br>3.87(d,J10.5,H-5')<br>4.12(d,J10.5,H-5)<br>6.68(d,J8.5,H-4)<br>6.78(d,J8.5,H-2')<br>7.78(d,J8.5,H-3)<br>8.47(d,J8.5,11-3') | 1.17(d,J6.0,H-11,11')<br>2.2–2.9(m,H-6,6',7,7')<br>3.67(s,H-13,13')<br>4.03(d,J10.5,H-5,5')<br>6.62(d,J8.5,H-2,2')<br>8.73(d,J8.5,H-3,3') |

| | IV | V | VI |
|---|---|---|---|
| Melting Point (°C.) | 207~208 | 201~202 | 204~205 |
| Mass | 638<br>579 | 638<br>579 | 638<br>579 |
| [α]$_D^{20}$ (pyridine) (°) | +198.4°(c 0.256) | +109.7°(c 0.259) | −125.1°(c 0.267) |
| λ$_{max}^{dioxane}$<br>nm (log ε) | 239(4.26)<br>267(4.21)<br>338(4.53) | 251(4.31)<br>264(4.29)<br>338(4.54) | 255(4.38)<br>338(4.51) |
| νmax cm⁻¹ (KBr) | 3550(free OH)<br>3450(H-bonded OH)<br>1735(aliphatic C=O)<br>1605(H-bonded C=O) | 3580(free OH)<br>3450(H-bonded OH)<br>1735(aliphatic C=O)<br>1610(H-bonded C=O) | 3580(free OH)<br>3450(H-bonded OH)<br>1755(aliphatic C=O)<br>1615(H-bonded C=O) |
| ¹H—NMR (pyridine) | 1.25(d,J6.0,11,11')<br>2.2–2.9(m,H-6,6',7,7')<br>3.56(s,H-13,13')<br>4.17(d,J10.5,H-5,5')<br>6.70(d,J8.5,H-4,4')<br>7.60(d,J8.5,H-3,3') | 1.15(d,J6.0,H-11')<br>1.26(d,J6.0,H-11)<br>2.1–2.9(m,H-6,6',7,7')<br>3.36(s,H-13)<br>3.59(s,H-13')<br>3.89(d,J10.5,H-5')<br>4.14(d,J10.5,H-5)<br>6.72(d,J8.5,H-4)<br>6.79(d,J8.5,H-2')<br>7.80(d,J8.5,H-3)<br>8.48(d,J8.5,H-3') | 1.19(d,J6.0,H-11,11')<br>2.2–2.9(m,H-6,6',7,7')<br>3.67(s,H-13,13')<br>4.05(d,J10.5,H-5,5')<br>6.65(d,J8.5,H-2,2')<br>8.82(d,J8.5,H-3,3') |

[1]Specific rotatory power was measured in pyridine by Na lamps at 20° C., and C (g/100 ml) was the concentration of the solution at a measurement.
[2]UV spectrum (nm) was measured in dioxane, and the logarithm of molar absorbancy index (log ε) was parenthesized.
[3]IR spectrum was measured by using KBr tablet.
free OH: free hydroxyl group
H-bonded OH: hydroxyl group having a hydrogen bond
aliphatic C=O: aliphatic carbonyl group
H-bonded C=O: carbonyl group having a hydrogen bond
[4]NMR spectrum for protons was shown by δ used in the U.S.A. and Canada, and δ = 10-τ.
s: singlet, d: doublet, m: multiplet

TABLE 2

Chemical Sifts (δc, TMS) in Pyridine -d₅
(Unit: ppm)

| Compound Number | C-1 | C-2 | C-3 | C-4 | C-4a | C-5 | C-6 | C-7 |
|---|---|---|---|---|---|---|---|---|
| I | 159.97 | 118.14 | 140.80 | 107.81 | 159.88 | 76.60 | 30.54 | 36.71 |
| IV | 160.04 | 118.19 | 140.78 | 107.84 | 159.90 | 76.63 | 30.58 | 36.79 |
| II | 159.83 | 118.29 | 141.85 | 107.92 | 159.59 | 76.57 | 30.47 | 36.72 |
| V | 159.92 | 118.39 | 141.80 | 107.95 | 159.72 | 76.65 | 30.56 | 36.80 |

| | C-8 | C-8a | C-9 | C-9a | C-10a | C-11 | C-12 | C-13 |
|---|---|---|---|---|---|---|---|---|
| I | 178.55 | 102.59 | 187.84 | 107.46 | 86.19 | 18.43 | 171.10 | 52.75 |
| IV | 178.64 | 102.59 | 187.78 | 107.51 | 86.27 | 18.46 | 171.17 | 52.76 |
| II | 178.52 | 102.32 | 187.65 | 107.43 | 85.85 | 18.40 | 170.92 | 52.72 |
| V | 178.57 | 102.44 | 187.71 | 107.54 | 86.08 | 18.43 | 171.03 | 52.54 |

| | C-1' | C-2' | C-3' | C-4' | C-4a' | C-5' | C-6' | C-7' |
|---|---|---|---|---|---|---|---|---|
| II | 162.02 | 109.85 | 141.85 | 116.01 | 157.20 | 76.02 | 30.96 | 36.72 |
| V | 162.12 | 109.87 | 141.95 | 116.14 | 157.32 | 76.13 | 31.02 | 36.80 |
| III | 162.06 | 110.20 | 143.14 | 116.06 | 157.38 | 76.37 | 31.05 | 36.72 |
| VI | 162.03 | 110.17 | 143.07 | 116.06 | 157.37 | 76.40 | 31.06 | 36.79 |

| | C-8' | C-8a' | C-9' | C-9a' | C-10a' | C-11' | C-12' | C-13' |
|---|---|---|---|---|---|---|---|---|
| II | 178.41 | 102.71 | 187.65 | 107.62 | 85.96 | 18.40 | 170.92 | 52.77 |
| V | 178.48 | 102.84 | 187.71 | 107.75 | 85.98 | 18.43 | 171.03 | 52.76 |
| III | 178.37 | 102.79 | 187.75 | 107.56 | 86.06 | 18.43 | 170.96 | 52.85 |
| VI | 178.44 | 102.76 | 187.69 | 107.59 | 86.09 | 18.41 | 170.98 | 52.82 |

TABLE 3-1

Coupling Constants ($J_{CH}$) in Pyridine -$d_5$
(Unit: Hz)

| Compound Number | Carbon Number | | | | | | | |
|---|---|---|---|---|---|---|---|---|
| | C-1 | C-2 | C-3 | C-4 | C-4a | C-5 | C-6 | C-7 |
| I | d<br>3J 9.9 | dd<br>2J 3.8<br>3J 7.9 | d<br>1J 159.3 | d<br>1J 165.0 | dd<br>2J 3.0<br>3J 11.4 | dm<br>1J 144 | dm<br>1J 131 | tm<br>1J 128 |
| II | d<br>3J 10.0 | dd<br>2J 3.7<br>3J 7.5 | d<br>1J 159.4 | d<br>1J 167.4 | dd<br>2J 3.2<br>3J 11.3 | dm<br>1J 144 | dm<br>1J 131 | tm<br>1J 127 |

| Compound Number | Carbon Number | | | | | | | |
|---|---|---|---|---|---|---|---|---|
| | C-8 | C-8a | C-9 | C-9a | C-10a | C-11 | C-12 | C-13 |
| I | t<br>1J 6.9 | t<br>3J 2.0 | d<br>4J about 1 | d<br>3J 5.0 | d<br>2J 3.8 | qm<br>1J 127 | dq<br>3Jd 3.8<br>3Jq 5.0 | q<br>1J 147.7 |
| II | bt | bt | bd | bd<br>3J about 5 | bd<br>2J about 4 | qm<br>1J 127 | dq<br>3Jd about 5<br>3Jq about 4 | q<br>1J 147.6 |

TABLE 3-2

Coupling Constants ($J_{CH}$) in Pyridine -$d_5$
(Unit: Hz)

| Compound Number | Carbon Number | | | | | | | | | | | | | | |
|---|---|---|---|---|---|---|---|---|---|---|---|---|---|---|---|
| | C-1' | C-2' | C-3' | C-4' | C-4a' | C-5' | C-6' | C-7' | C-8' | C-8a' | C-9' | C-9a' | C-10a' | C-11' | C-12' | C-13' |
| III | dd<br>2J 2.0<br>3J 11.3 | d<br>1J<br>163.8 | d<br>1J<br>164.3 | dd<br>2J 3.8<br>3J 8.2 | d<br>3J<br>10.1 | dm<br>1J<br>142 | dm<br>1J 130 | tm<br>1J<br>129 | t<br>3J<br>7.5 | bt<br>3J<br>about 2 | bs | d<br>3J 5.1 | d<br>2J 4.4 | qm<br>1J<br>128 | dq<br>3Jd 5.0<br>3Jq 3.8 | q<br>1J<br>148.1 |
| IV | dd<br>2J about 2<br>3J 11.2 | d<br>1J<br>163.7 | d<br>1J<br>164.7 | dd<br>2J 3.7<br>3J 7.5 | d<br>3J<br>10.6 | dm<br>1J<br>144 | dm<br>1J 131 | tm<br>1J<br>127 | bt | bt | bs | bd<br>3J<br>about 5 | bd<br>2J<br>about 4 | qm<br>1J<br>127 | dq<br>3Jd about 5<br>3Jq about 4 | q<br>1J<br>147.5 |

1J: coupling constant of 1,1-position such as 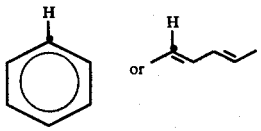 or

2J: coupling constant of 1,2-position such as 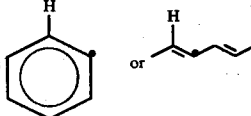 or

3J: coupling constant of 1,3-position such as 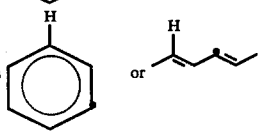 or d: doublet,
dd: double doublet,
dq: double quadruplet,
dm: double multiplet,
t: triplet,
tm: triple multiplet,
q: quadruplet,
qm: quadruple multiplet,
bs: broad singlet,
bd: broad doublet,
bt: broad triplet

TABLE 4

$^{13}C-^{13}C$ Spin-Spin Couplings

| Compound Number | C—C Couplings | 1Jcc (Hz) | Average Enrichment (%) |
|---|---|---|---|
| I | C-1:C-2 | 69.3 ± 0.0 | 0.09 ± 0.01 |
| | C-2:C-3 | 58.6 ± 0.3 | 0.09 ± 0.04 |
| | C-3:C-4 | 57.2 ± 0.4 | 0.09 ± 0.03 |
| | C-4:C-4a | 72.3 ± 0.2 | 0.08 ± 0.03 |
| | C-5:C-10a | 39.7 ± 0.3 | 0.17 ± 0.05 |
| | C-6:C-11 | 36.0 ± 0.3 | 0.18 ± 0.02 |
| | C-8:C-8a | 70.9 ± 0.1 | 0.16 ± 0.01 |

TABLE 4-continued $^{13}C-^{13}C$ Spin-Spin Couplings

| Compound Number | C—C Couplings | 1Jcc (Hz) | Average Enrichment (%) |
|---|---|---|---|
| | C-9:C-9a | 55.2 ± 0.0 | 0.18 ± 0.02 |
| III | C-1:C-2 | 67.4 ± 0.1 | 0.08 ± 0.02 |
| | C-2:C-3 | 58.8 ± 0.7 | 0.11 ± 0.01 |
| | C-3:C-4 | 58.1 ± 0.3 | 0.09 ± 0.01 |
| | C-4:C-4a | 72.3 ± 0.3 | 0.09 ± 0.02 |
| | C-5:C-10a | 40.9 ± 0.3 | 0.16 ± 0.04 |
| | C-6:C-11 | 36.1 ± 0.3 | 0.19 ± 0.02 |

TABLE 4-continued

| | $^{13}C$—$^{13}C$ Spin-Spin Couplings | | |
|---|---|---|---|
| Compound Number | C—C Couplings | 1Jcc (Hz) | Average Enrichment (%) |
| | C-8:C-8a | 70.8 ± 0.0 | 0.16 ± 0.01 |
| | C-9:C-9a | 55.6 ± 0.2 | 0.19 ± 0.03 |

[1] 1Jcc (Hz) is coupling constant of C—C couplings, and data accuracy is ±0.6 Hz.
[2] Average enrichment was calculated by using the formula described in "C-13 NMR Biosynthetic Studies" by A. G. McInnes, J. A. Walter, Jec, L. C. Wright and L. C. Vining in topics "In C-13 NMR Spectroscopy" by G. C. Levy (published by Willey, New York City, U.S.A. Vol. 2, 123-178, 1976).

TABLE 5-1

| | Deuterium Isotope Effect on $^{13}$C Chemical Shifts | | | |
|---|---|---|---|---|
| Compound Number | Carbon Number | δc(OD) | δc(OH) | δc(OD)−δc(OH) |
| III | C-1 | 161.28 | 161.50 | −0.22 |
| | C-2 | 110.08 | 110.18 | −0.10 |
| | C-3 | 141.56 | 141.59 | −0.03 |
| | C-4 | 115.43 | 115.41 | +0.02 |
| | C-4a | 155.89 | 155.86 | +0.03 |
| | C-5 | 76.46 | 76.60 | −0.14 |
| | C-6 | 29.08 | 29.16 | −0.08 |
| | C-7 | 36.19 | 36.36 | −0.17 |
| | C-8 | 176.51 | 177.22 | −0.71 |
| | C-8a | 101.63 | 101.62 | +0.01 |
| | C-9 | 187.09 | 187.02 | +0.07 |
| | C-9a | 106.98 | 106.96 | +0.02 |
| | C-10a | 85.00 | 84.97 | +0.03 |
| | C-11 | 18.15 | 18.15 | 0.00 |
| | C-12 | 170.09 | 170.09 | 0.00 |
| | C-13 | 53.18 | 53.18 | 0.00 |

TABLE 5-2

| | Deuterium Isotope Effect on $^{13}$C Chemical Shifts | | | |
|---|---|---|---|---|
| Compound Number | Carbon Number | δc(OD) | δc(OH) | δ(OD) − δc(OH) |
| VII | C-1 | 159.14 | 159.30 | −0.16 |
| | C-2 | 118.11 | 118.17 | −0.06 |
| | C-3 | 140.44 | 140.45 | −0.01 |
| | C-4 | 107.81 | 107.78 | +0.03 |
| | C-4a | 158.35 | 158.29 | +0.06 |
| | C-5 | 76.10 | 76.10 | 0.00 |
| | C-6 | 28.43 | 28.42 | +0.01 |
| | C-7 | 35.92 | 36.02 | −0.10 |
| | C-8 | 176.16 | 176.88 | −0.72 |
| | C-8a | 101.59 | 101.55 | +0.04 |
| | C-9 | 187.11 | 187.00 | +0.11 |
| | C-9a | 106.75 | 106.70 | +0.05 |
| | C-10a | 82.76 | 82.72 | +0.04 |
| | C-11 | 17.46 | 17.44 | +0.02 |
| | C-12 | 169.77 | 169.76 | +0.01 |
| | C-13 | 53.40 | 53.39 | +0.01 |
| | C-14 | 159.94 | 159.97 | −0.03 |

[1] δc(OD) is a chemical shift of deuterium isotope.
[2] Minus (−) means the change to high magnetic field and plus (+) means the change to low magnetic field.

The configurations of Compounds II, III, V and VI were identified with those shown in FIGS. 2, 3, 5 and 6 by the above described physical properties and circular dichroism spectra of FIGS. 11 to 13. Namely, Compound II is 2,4'-linked secalonic acid A, Compound III is 4,4'-linked secalonic acid A, Compound V is 2,4'-linked secalonic acid D and Compoun VI is 4,4'-linked secalonic acid D. The identification procedure will now be given below in more detail.

NMR spectra for protons of six compounds in Table 1 have a strong resemblance among them, and show that all these compounds are isomers or enantiomers with one another. The number of NMR signals of Compound II and V are two times as many as those of Compounds III and VI. Thus, Compounds II and V are considered to have an asymmetrical structure, and Compounds III and VI are considered to have a symmetrical structure as Compounds I and IV. The spectrum of Compound II shows the 4-hydrogen xanthone group of Compound I and Compound III, and the spectrum of Compound V is a combination of the spectra of Compound IV and Compound VI.

Further, all the NMR spectra exhibit an AB pattern spectrum indicating that the aromatic protons are adjacent to one another. The chemical shifts of the aromatic protons are quite different from other protons, and thus it may be considered that the equilibrium state where three isomers are present as a mixture is caused by some change in the aromatic rings.

Figure 1:
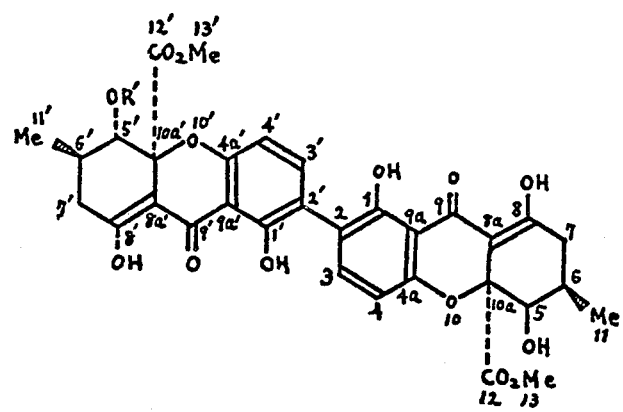
FIG. 1 is a constitutional formula of secalonic acid A having a 2,2'-linkage, "Compound I".
Figure 2:
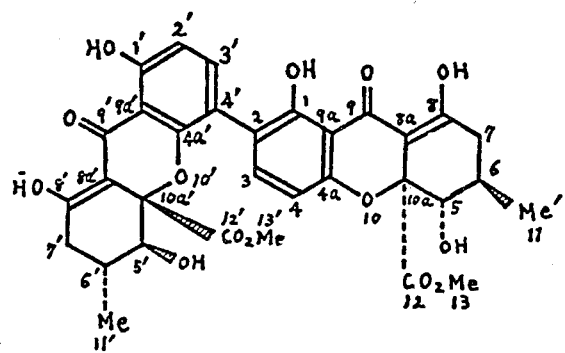
FIG. 2 is a constitutional formula of secalonic acid A having a 2,4'-linkage, "Compound II".
Figure 3:
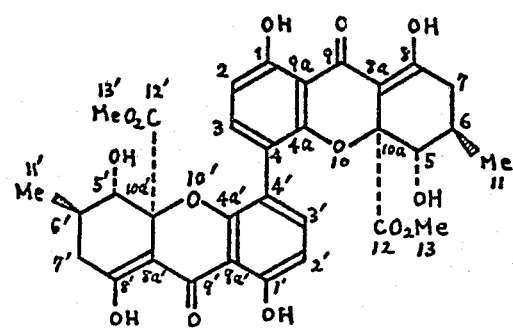
FIG. 3 is a constitutional formula of secalonic acid A having a 4,4'-linkage, "Compound III".
Figure 4:
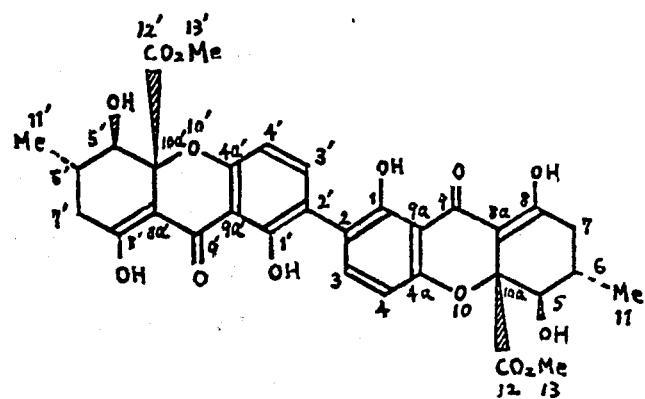
FIG. 4 is a constitutional formula of secalonic acid D having a 2,2'-linkage, "Compound IV".
Figure 5:
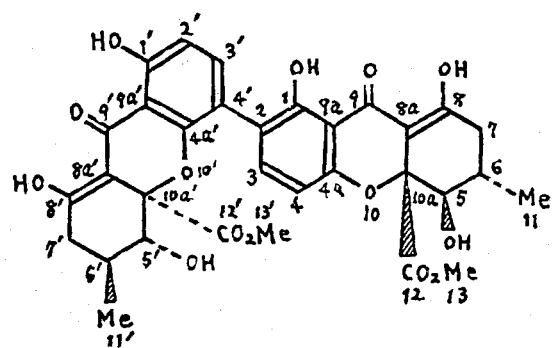
FIG. 5 is a constitutional formula of secalonic acid D having a 2,4'-linkage, "Compound V".
Figure 6:
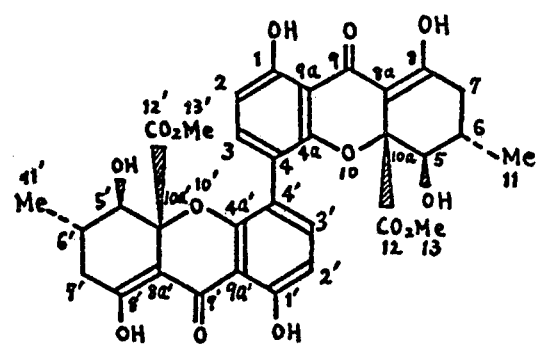
FIG. 6 is a constitutional formula of secalonic acid D having a 4,4'-linkage, "Compound VI".
Figure 7:
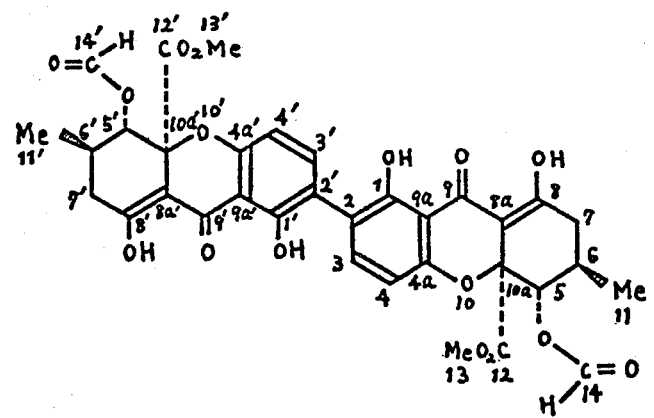
FIG. 7 is a constitutional formula of a diformyl derivative of secalonic acid A having a 2,2'-linkage, "Compound VII".

The chemical shifts for carbons in Compound I are set forth in Table 2. Since Compound I has a symmetrical structure, only 16 signals can be observed in the $^{13}$C-NMR spectrum. The signals of carbons can be attributed in the following manner. Carbon numbers are shown in FIG. 1.

Each signal is attributed by the multiplicity for carbon-hydrogen couplings in the high resolution $^{13}$C-NMR spectra, their coupling constants and chemical shifts.

The signals for carbons linked with hydrogen, i.e. carbon number of C-3, C-4, C-5, C-6, C-7, C-11 and C-13, can be easily identified. Carbon number C-4 is distinguishable from C-3, since the signal for C-4 shifted to a high magnetic field compared with C-3 by the influence of the adjacent oxygen.

As will be expected from "Carbon-13 NMR Spectroscopy" by J. B. Stothers (published by Academic Press, New York City, United States, 1976), the signals of C-8 and C-9 of β-diketone shift to an extremely low magnetic field. On the other hand, the signal of C-8a shifts to a high magnetic field. Further, C-8 is distantly coupled with H-7, but C-9 is not coupled. As a result, C-8 is distinguishable from C-9.

The signal of C-12 can be easily distinguished from that of C-9 of carbonyl group, since C-12 is distantly linked with H-5 and the methyl group of C-13.

Both C-1 and C-4a give signals at a low magnetic field by influence of the adjacent oxygen and their chemical shifts are very similar to each other. Accordingly, often it is difficult to distinguish their signals from each other, but C-1 could be distinguished from C-4a by a difference in linkages, since C-1 is distantly coupled with only H-3. Namely, the signal at 159.97 ppm is changed to doublet (9.9 Hz) and the signal at 159.88 ppm is changed to a double doublet (3.0 and 11.4 Hz) in the high resolution $^{13}$C-NMR spectra. It can be proved from the above described result that the signal of 159.97 ppm for C-1 is coupled with the meta-position hydrogen and the signal of 159.88 ppm for C-4a is coupled with the hydrogens at the meta- and ortho-positions.

It is confirmed by X-ray diffractiometry that the linkage position of the dimer of Compound I is 2,2'-position. Consequently, the signal at 159.97 ppm is assigned to C-1 and the signal at 159.88 ppm is assigned to C-4a.

The signal of C-9a is shifted to a higher magnetic field than that of C-2 by the influence of the oxygen adjacent to C-1 and C-4a, and the signal of C-9a is distantly coupled with only H-4 whereas C-2 is distantly coupled with H-4 and H-3'. Thus, the signals of C-9a and C-2 can be attributed from the difference of their couplings.

The signal of C-10a could be identified since it is shifted to a high magnetic field by the influence of the adjacent oxygen and carbomethoxy group. Further the signal is changed to a doublet in the high resolution spectrum due to the distant coupling with H-5.

The same method of assignment can be applied to the attribution of Compound IV which is an enantiomer of Compound I.

When the same method for assigning chemical shifts of the above described known compounds is applied to the diagnosis of new Compound III, the chemical shifts relevant to C-1 and C-4a are observed at 162.06 ppm and 157.38 ppm, respectively. In the high resolution $^{13}C-^{1}H$ coupling at 162.06 ppm exhibits a double doublet (2.0 and 11.3 Hz) and the signal at 157.38 ppm exhibits a doublet (10.1 Hz). Thus, it is understood that the signal at 162.06 ppm is coupled with the hydrogens at the meta- and ortho-positions, and that the signal at 157.38 ppm is coupled with the meta-position hydrogen.

From the above-described result, two structures may be proposed concerned with regard to Compound III. One is the 2,2'-linked dimer whose signals at 162.06 ppm and 157.38 ppm are assigned to C-4a and C-1, respectively. The other is the 4,4'-linked dimer whose signals at 162.06 ppm and 157.38 ppm are assigned to C-1 and C-4a, respectively. To determine the structure, "Prog. Nucl. Magn. Reson. Spectros, 1969,3,63" published by H. Batiz-Hernandez and R. A. Bernheim are referred to. According to the reference, though both C-1 and C-4a carbons have oxygen at the adjacent positions, the oxygen adjacent to C-1 carbon is the oxygen of a hydroxyl group and the hydrogen of the hydroxyl group is easily substituted with deuterium, therefore signals for the carbon having a hydroxyl group is shifted to a high magnetic field. The method for preparing samples for $^{13}C$-NMR spectroscopy will now be explained below.

Since Compound I for comparison is insoluble in chloroform, the diformyl derivative of Compound I which is soluble in chloroform is prepared in the following method.

1.004 g of Compound I was dissolved in 400 ml of formic acid under heating. After the solution was filtered, the filtrate was left to stand at room temperature for 2 days. The formic acid was removed from the filtrate by a reduced pressure distillation, and completely removed in a desiccator under reduced pressure for all day. The product thus obtained was dissolved in chloroform and unreacted Compound I was removed by filtration. Then the filtrate was adsorbed on silicic acid powder and dried. The silicic acid powder was suspended in benzene and the suspension was pored into a column filled with silicic acid. Mixed solvent of benzene and ethyl acetate was used as a developing agent. The diformate of Compound I was eluted when the volume ratio of benzene to ethyl acetate was 8:1 and the monoformate of Compound I was obtained when the volume ratio was 4:1. The yield of the monoformate was 338 mg and that of the diformate was 421 mg.

The diformate of Compound I (Compound VII) as obtained in the above described step and Compound III were substituted with deuterium as follows. The $^{13}C$-NMR spectra of Compounds VII and III were measured in deuterium substituted chloroform as a solvent. Then the solutions were added to deuterium substituted methanol and well mixed. After the solutions were left to stand for several minutes, helium gas having a low content of water was introduced to the solutions under heating to thoroughly remove methanol from the solutions. The degree of deuterium substitution of the solution was measured by $^{1}H$-NMR spectroscopy, and as a result, at least 80% of hydrogen in the hydroxyl groups was substituted with deuterium. To the solutions were added again 0.1 ml of deuterium substituted methanol and well mixed. After the solutions were left to stand for several minutes, helium gas was introduced to the solution to thoroughly remove methanol therefrom. In this second substitution, at least 95% of deuterium substitution was occurred. After the substitution was repeated further three times, the solutions were dried in a desiccator filled with phosphorus pentoxide as a drying agent at 60° C. under reduced pressure for 3 hours to entirely remove moisture. The solutions were placed in tubes and helium gas was introduced into the tubes to remove air. After air in the tubes was thoroughly replaced by helium gas, the $^{1}H$-NMR spectra of the solution was measured. Any hydrogen unsubstituted with deuterium in the hydroxyl groups was not observed. In this deuterium substitution, the hydrogens except the ones in the hydroxyl groups were not substituted with deuterium. The chemical shifts of deuterium substituted Compounds III and VII thus obtained were measured by $^{13}C$-NMR spectroscopy is deuterium substituted chloroform, and shown in Tables 5-1 and 5-2. Further, changes of the chemical shifts were calculated and shown in Tables 5-1 and 5-2. Changes to a high magnetic field are represented by minus sign (—) and changes to a low magnetic field are shown by plus sign (+).

As shown in Table 5-2, the signal of Compound VII at 176.88 ppm which is assigned to C-8 is shifted to a high magnetic field to the greatest extent and the signal at 159.30 ppm is assigned to C-1 is the next one greatly shifted to a high magnetic field. In the case of Compound III, the signal at 177.22 ppm is shifted to a high magnetic field to the greatest extent and the signal at 161.50 ppm is the next one greatly shifted to a high magnetic field. Accordingly, signals at 177.22 ppm and 161.50 ppm are assigned to C-8 and C-1, respectively, and the signals of Compound III at 178.37 ppm and 162.06 ppm as shown in Table 2 are assigned to C-8 and C-1, respectively. Without other probabilities are not considered. Thus, Compound III is confirmed to have 4,4'-linkage.

A biosynthetic identification procedure will be given below as another method of the structure of secalonic acids.

In 1 l of a culture solution of *Pyrenochaeta terrestris* C-44-1 capable of producing 2,2'-linked secalonic acid A (Compound I) after 3 days cultivation was added 1,2-$^{13}C$ labeled sodium acetate having a concentration of at least 90% to give a solution having a final concentration of 5 mM, and the cultivation was further continued for 7 days. After 10 days in total the microorganism was separated from the cultivation liquid by filtration and Compound I was extracted with acetone from the microorganism. Fractions of Compound I were collected and concentrated, and then Compound I was recrystallized from a 2:1 volume ratio mixed solvent of ethyl acetate and ethanol to give 683 mg of 1,2-$^{13}C$ labeled Compound I. The labeled Compound I was measured by $^{13}C$-NMR spectroscopy.

After the measurement, 683 mg of Compound I were dissolved into 10 ml of pyridine and the solution was left to stand at 45° C. for 4 days. The solution was purified by the above described column partition chromatography to give 190 mg of 1,2-$^{13}C$ labeled Compound II and 182 mg of 1,2-$^{13}C$ labeled Compound III. The $^{13}C$-NMR signals of 1,2-$^{13}C$ labeled Compound I and 1,2-

$^{13}$C labeled Compound III obtained in the above step are shown in Table 4.

The signal of Compound I at 159.97 ppm assigned to C-1 exhibited a doublet by $^{13}$C-$^{13}$C spin-spin couplings and the coupling constant was 69.3 Hz. Further, the signal at 118.4 ppm assigned to C-2 was coupled with C-1 and C-3 to show a double doublet with the coupling constants of 69.3 Hz and 58.9 Hz. Accordingly, it can be proved that C-2 is coupled with C-1 and that the carbon at the linkage position of the dimer is adjacent to C-1. Thus the linkage of Compound I is 2,2′-linkage.

This procedure is employed to confirm that the linkage of Compound III is 4,4′-linkage. The procedure is as follows.

As shown in Table 2, chemical shifts for carbon other than in the A-ring of Compound III are in accord with to those of Compound I. Therefore, chemical shifts for each carbon can be easily assigned in correspondence to those of Compound I. Further, this assignment can be confirmed by the $^{13}$C-$^{1}$H spin-spin coupling mode and their coupling constants obtained by high resolution $^{13}$C-NMR spectroscopy, which is shown in Tables 3-1 and 3-2.

The chemical shift for C-9a in the A-ring of Compound III is easily and exactly assigned by the value of $^{13}$C-$^{13}$C spin-spin coupling with the already assigned C-9 in Table 4. Two carbons adjacent to one oxygen can be assigned by the above described deuterium substitution. More specifically, the signal at 162.06 ppm having a hydroxyl group is assigned to C-1 and as a result, the signal at 157.38 ppm is assigned to C-4a. From each signal of 143.14 ppm and 110.20 ppm, C-1 and C-4a are confirmed to be linked with one hydrogen, respectively, by high resolution $^{13}$C-NMR spectroscopy. Accordingly, the remaining signal at 116.06 ppm was assigned to the carbon at the linkage position of the dimer. Further, this signal was exhibits a double doublet (3.8 Hz and 8.2 Hz) in the high resolution $^{13}$C-NMR spectrum, and therefore the carbon is coupled with the hydrogen in the meta- and ortho-positions. This coupling mode and coupling constants are very similar to those of the carbon C-2 the linkage position of Compound I. However, as shown in Table 4, the signal at 116.06 ppm exhibits a doublet of $^{13}$C-$^{13}$C spin-spin coupling and its coupling constants are 72.0 Hz and 58.4 Hz. Accordingly, it is known that the signal at 116.06 ppm is not coupled with C-4a assigned already. Therefore, the signal at 116.06 ppm is assigned to C-4 and the carbon at the linkage position of the dimer of Compound III is confirmed to C-4. As the result, the carbons linked with hydrogens are C-2 and C-3, and the signals at 143.14 ppm and 110.20 ppm are assigned to C-3 and C-2, respectively, in correspondence to Compound I. This assignment is confirmed by the $^{13}$C-$^{13}$C spin-spin coupling constants in Table 4.

The structures of other secalonic acids can be determined in the same manner as above described. As the result of fixing the structure of Compounds I and III, Compound II is determined to be 2,4′-linked secalonic acid A. Furthermore, the result of determining the structure of Compound II is also supported by the $^{1}$H-NMR values and the $^{13}$C-NMR values as shown in Tables 1, 2 and 3-1.

A further method of determining the structure of secalonic acid uses the relation of the enantiomers. Two compounds which are in relation of an enantiomer, for example Compounds I and IV, must have the same measurement values expecting the optical rotatory powers. These optical rotatory powers shown the same absolute value and differ from each other only in sign. Accordingly, if this can be proved experimentally, two compounds are confirmed to be an enantiomer.

Both Compounds V and VI obtained by rearranging Compound IV, had a basic peak ion at 638 in mass spectra, although their high resolution mass spectra are not measured. Therefore, the molecular structures of Compounds V and VI are considered to be identical with Compound I. This can be also confirmed by the number of hydrogen and carbons and their chemical shifts in the $^{1}$H- or $^{13}$C-NMR spectra.

Measurement values of melting points, ultraviolet absorptions, infrared absorptions, $^{1}$H-NMR and $^{13}$C-NMR in Tables 1 and 2 are identical with respect to Compounds I and IV; Compounds II and V; and Compounds III and VI, within the experimental error. Accordingly, two compounds in each combination are considered to be the same compound or to be enantiomers. The absolute value of specific rotatory powers in pyridine in Table 2 are also identical within the experimental error in the above described combinations but the signs are different. Therefore, two compounds in each combination can be decided to be enantiomers with each other. Further, this relation is confirmed by the circular dichroism spectra in dioxane as shown in FIGS. 11 to 13.

As the result, Compound IV which is the enantiomer of Compound I has a 2,2′-linkage; Compound V which is the enantiomer of Compound II has a 2,4′-linkage and Compound VI which is the enantiomer of Compound III has a 4,4′-linkage.

Novel secalonic acids of this invention are useful as an antibacterial agent. The MIC (μm/ml) data of 2,4′-linked secalonic acid D, 4,4′-linked secalonic acid D and 2,2′-linked secalonic acid D are shown in Table 6.

TABLE 6

| | MIC (μg/ml) | | |
|---|---|---|---|
| | 2,4′-SD | 4,4′-SD | 2,2′-SD |
| *Sarcina lutea* ATCC 9341 | 12.5 | 3.1 | >100 |
| *Bacilus subtilis* CPI 219 | 50 | 12.5 | >100 |
| *Corynebacterium diphtheriae* P.W.8 | 12.5 | 6.3 | 50 |
| *Micrococcus flavis* ATCC 10240 | 25 | 12.5 | 100 |
| *Trichophyton mentagrophytes* IAM 8051 | 3.1 | 1.6 | 12.5 |

What is claimed is:

1. A secalonic acid in substantially pure form having a 2,4′-linkage of the formula (I) or a 4,4′-linkage of the formula (II),

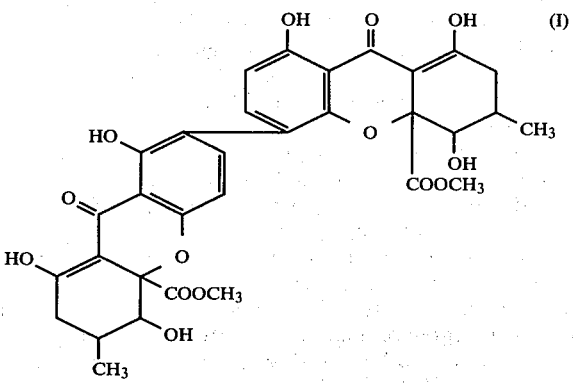

-continued

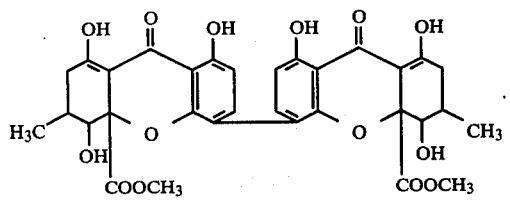

(II)

2. The compound of claim 1, wherein the secalonic acid is secalonic acid A.

3. The compound of claim 1, wherein the secalonic acid is secalonic acid D.

4. The compound of claim 1, wherein the secalonic acid is secalonic acid A having a 4,4'-linkage and having a positive specific rotatory power in pyridine of 125.7°.

5. The compound of claim 1, wherein the secalonic acid is secalonic acid D having a 4,4'-linkage and having a negative specific rotatory power in pyridine of 125.1°.

* * * * *